(12) United States Patent
Laubach et al.

(10) Patent No.: US 11,051,966 B2
(45) Date of Patent: *Jul. 6, 2021

(54) THERMOFORMABLE SPLINT STRUCTURE WITH INTEGRALLY ASSOCIATED OXYGEN ACTIVATED HEATER AND METHOD OF MANUFACTURING SAME

(71) Applicant: Rechargeable Battery Corporation, College Stations, TX (US)

(72) Inventors: Adam Laubach, Kingwood, TX (US); Alberto Macias Barrio, College Station, TX (US)

(73) Assignee: RECHARGEABLE BATTERY CORPORATION, College Station, TX (US)

( * ) Notice: Subject to any disclaimer, the term of this patent is extended or adjusted under 35 U.S.C. 154(b) by 581 days.

This patent is subject to a terminal disclaimer.

(21) Appl. No.: 15/589,190

(22) Filed: May 8, 2017

(65) Prior Publication Data
US 2018/0055677 A1  Mar. 1, 2018

Related U.S. Application Data

(63) Continuation of application No. 14/206,252, filed on Mar. 12, 2014, now Pat. No. 9,642,736.

(51) Int. Cl.
*A61F 5/058* (2006.01)
(52) U.S. Cl.
CPC .......... *A61F 5/058* (2013.01); *A61F 5/05825* (2013.01); *Y10T 29/49826* (2015.01)

(58) Field of Classification Search
CPC ........ A61L 15/12; A61L 15/125; A61L 15/14; A61L 15/07; A61L 15/10; A61L 27/44;
(Continued)

(56) References Cited

U.S. PATENT DOCUMENTS

| 2,759,475 A | 8/1956 | Van Swaat |
| 3,490,444 A | 1/1970 | Larson |

(Continued)

FOREIGN PATENT DOCUMENTS

| CN | 86100407 A | 7/1986 |
| CN | 86105955 A | 7/1987 |

(Continued)

OTHER PUBLICATIONS

International Search Report and Written Opinion in related International Application No. PCT/US2015/020150 dated Jun. 12, 2015, 10 pages.

(Continued)

*Primary Examiner* — Ophelia A Hawthorne
(74) *Attorney, Agent, or Firm* — Schroeder Intellectual Property Law Group, LLC

(57) ABSTRACT

An integrated thermoformable splint and heater and method for manufacturing same includes a thermoplastic material and an oxygen activated heater operatively associated with the thermoplastic material. The integrated thermoformable splint and heater are sealed within an oxygen impermeable housing. Oxygen is allowed to activate the heater either by removing the assembly from the sealed housing, or, by displacement of a removable seal that will allow oxygen to penetrate a porous region in the housing, and, in turn, come into contact with the heater.

18 Claims, 2 Drawing Sheets

(58) Field of Classification Search
CPC .......... A61F 5/0111; A61F 5/01; A61F 13/04;
A61F 5/058; A61F 5/05841; A61F
5/0102; A61F 5/05825; A61F 5/0118;
A61F 5/0127; A61F 5/05866; A61F
5/055; A61F 5/14; A61F 7/03; A61F
13/041; A61F 13/046; A61F 5/0123;
A61F 5/05; A61F 2007/0001; A61F
2210/0071; A61F 2210/0076; A61F 5/02;
A61F 5/028; A61F 5/0585; A61F
2002/608; A61F 2002/6614; A61F
2007/0089; A61F 7/00; A61F 7/032;
A61F 7/08; C08L 2203/02; Y10T
29/49826; Y10T 29/49; Y10T 29/49002;
Y10T 29/49412; Y10T 29/49828; Y10T
29/49908; Y10T 156/10; Y10T 29/481;
Y10T 29/4921; Y10T 29/49227; Y10T
29/4984; Y10T 29/49822; Y10T
29/49837; Y10T 403/34; Y10T 83/04;
F24J 1/00
See application file for complete search history.

(56) References Cited

U.S. PATENT DOCUMENTS

| | | | |
|---|---|---|---|
| 3,798,799 | A | 3/1974 | Hanson et al. |
| 3,809,600 | A | 5/1974 | Larson |
| 4,083,127 | A | 4/1978 | Hanson |
| 4,708,130 | A | 11/1987 | Grudem et al. |
| 4,778,717 | A | 10/1988 | Fitchmun |
| 4,821,524 | A | 4/1989 | Kostyal et al. |
| 4,874,656 | A | 10/1989 | Rantanen |
| 5,042,464 | A | 8/1991 | Skwor et al. |
| 5,310,584 | A | 5/1994 | Jacoby |
| 5,366,491 | A | 11/1994 | Ingram et al. |
| 5,554,104 | A | 9/1996 | Grim |
| 5,652,053 | A | 7/1997 | Liegeosis |
| 5,879,378 | A | 3/1999 | Usui |
| 5,919,547 | A | 7/1999 | Kocher et al. |
| 6,248,257 | B1 | 6/2001 | Bell et al. |
| 7,311,866 | B1 | 12/2007 | Stearns et al. |
| 7,722,782 | B2 | 5/2010 | Coffey et al. |
| 8,137,392 | B2 * | 3/2012 | Friedensohn ............ A61F 7/03 602/7 |
| 9,004,059 | B2 | 4/2015 | Sesock et al. |
| 9,642,736 | B2 * | 5/2017 | Laubach ............ A61F 5/05825 |
| 9,872,795 | B2 | 1/2018 | Laubach et al. |
| 2002/0072696 | A1 | 6/2002 | Varn |
| 2002/0077401 | A1 | 6/2002 | Chaudhary et al. |
| 2004/0006950 | A1 | 1/2004 | Knoerzer et al. |
| 2004/0042965 | A1 | 3/2004 | Usui et al. |
| 2004/0211698 | A1 | 10/2004 | Mak |
| 2005/0187502 | A1 | 8/2005 | Krempel et al. |
| 2007/0007229 | A1 | 1/2007 | Yousif |
| 2007/0020412 | A1 | 1/2007 | Kumamoto et al. |
| 2007/0142883 | A1 * | 6/2007 | Quincy, III ............... A61F 7/03 607/96 |
| 2007/0202284 | A1 | 8/2007 | True |
| 2008/0154164 | A1 | 6/2008 | Sheehan et al. |
| 2008/0202490 | A1 | 8/2008 | Dodo |
| 2008/0251062 | A1 | 10/2008 | Dodo |
| 2008/0262400 | A1 | 10/2008 | Clark et al. |
| 2008/0319362 | A1 | 12/2008 | Joseph |
| 2009/0072189 | A1 | 3/2009 | Wong et al. |
| 2010/0089381 | A1 | 4/2010 | Bolmer et al. |
| 2010/0163011 | A1 | 7/2010 | Tinker et al. |
| 2010/0217168 | A1 | 8/2010 | King et al. |
| 2010/0278454 | A1 | 11/2010 | Huffer |
| 2010/0326418 | A1 | 12/2010 | Sesock et al. |
| 2011/0081460 | A1 | 4/2011 | Becraft et al. |
| 2011/0103718 | A1 | 5/2011 | Bosman |
| 2011/0204054 | A1 | 8/2011 | Huffer |
| 2012/0101417 | A1 | 4/2012 | Joseph |
| 2012/0145189 | A1 | 6/2012 | Knopow et al. |
| 2012/0184672 | A1 | 7/2012 | Riscanu et al. |
| 2012/0203155 | A1 | 8/2012 | Watson |
| 2013/0174835 | A1 | 7/2013 | Tinker et al. |
| 2013/0345649 | A1 | 12/2013 | Stockley, III et al. |
| 2014/0102435 | A1 | 4/2014 | Sesock et al. |
| 2014/0109889 | A1 | 4/2014 | Pedicini et al. |
| 2014/0109890 | A1 | 4/2014 | Pedicini et al. |
| 2015/0059729 | A1 | 3/2015 | Tinker et al. |
| 2016/0161149 | A1 | 6/2016 | Laubach et al. |
| 2016/0279638 | A1 | 9/2016 | Beckerdite et al. |

FOREIGN PATENT DOCUMENTS

| | | |
|---|---|---|
| CN | 1251511 A | 4/2000 |
| CN | 2379111 Y | 5/2000 |
| CN | 1271264 A | 10/2000 |
| CN | 101325932 A | 12/2008 |
| CN | 101330887 A | 12/2008 |
| CN | 102387818 A | 3/2012 |
| CN | 102421394 A | 4/2012 |
| CN | 103040550 A | 4/2013 |
| JP | S61-268428 A | 11/1986 |
| JP | H09-234241 A | 9/1997 |
| JP | 2005-224314 A | 8/2005 |
| JP | 2008-512170 A | 4/2008 |
| JP | 2009-519747 A | 5/2009 |
| JP | 2009-519753 A | 5/2009 |
| JP | 2012-518516 A | 8/2012 |
| JP | 2012-520099 A | 9/2012 |
| JP | 2012-207170 A | 10/2012 |
| JP | 2012-527321 A | 11/2012 |
| WO | 01/19302 | 3/2001 |
| WO | 2007/034444 A1 | 3/2007 |
| WO | 2010/099130 A1 | 9/2010 |
| WO | 2016/164540 | 10/2016 |

OTHER PUBLICATIONS

International Search Report and Written Opinion in International Application No. PCT/US2015/1020153 dated Jun. 18, 2015, 11 pages.

Dellarocca, P.; "Air-Activated Ration Heaters;" Proceedings of the Army Science Conference (26th); dated Dec. 2008.

CookPake®—Self-Heating Packaging Technology for Food; RCE Technologies; dated Aug. 21, 2013.

Exothermic Nanocomposite for Self-Contained Ration Heater; U.S Army NSRDEC—NNI Scientific Accomplishments; dated 2009.

"U.S. Market for Packaging Barrier Resins to Reach 8.6 Billion Pounds by 2009" [online] [retrieved Mar. 17, 2015]. Retrieved from the internet: <URL: http://www.ien.com/article/us-market-packaging/8562>. 6 pages.

Unpublished U.S. Appl. No. 15/564,460, filed Oct. 5, 2017, previously published as WO2016/164540 to Beckerdite, et al.

"PTFE Thermofoil Heaters" Technical Specification PTFE, MINCO 2008.

European Search Report in EP application No. 15762226.7 dated Dec. 5, 2017, 7 pages.

European Search Report in EP application No. 15761672.3 dated Dec. 5, 2017, 7 pages.

Unpublished U.S. App. No. 15/875,094 filed Jan. 19, 2018.

* cited by examiner

THERMOFORMABLE SPLINT STRUCTURE WITH INTEGRALLY ASSOCIATED OXYGEN ACTIVATED HEATER AND METHOD OF MANUFACTURING SAME

CROSS REFERENCE TO RELATED APPLICATIONS

The present application is a continuation of U.S. patent application Ser. No. 14/206,252 filed Mar. 12, 2014, the contents of which are fully incorporated herein by reference.

FIELD OF THE INVENTION

The invention relates to a portable thermoformable splint structure in combination with a heater that utilizes atmospheric oxygen as a source of a chemical reactant for an exothermic reaction.

BACKGROUND OF THE INVENTION

Thermoformable materials have been used in association with casts and splints for medical purposes for several years. Indeed, such materials offer several benefits over conventional "plaster" casts and splints, such as faster set times, eliminating the lengthy application process associated therewith and the dampness inflicted on the patients skin.

U.S. Pat. No. 4,778,717 is directed to a specific structure for a thermoplastic, thermoformable composite.

U.S. Pat. No. 5,652,053 discloses utilizing a molecular or intermolecular combination of materials comprised of an inter-penetrating polymer network so as to cause the combined structure to transfer from an amorphous state to a viscoelastic and rubbery state. While such a structure may provide some support to a user, it is not effective when a ridged support is desired such as is typically the case when a splint or cast is desired.

U.S. Pat App. Nos. 20080319362 and 20120101417 both disclose a thermoformable cast or splint that can be used in association with an exothermic heating reaction for causing a thermoplastic material to go from a relatively rigid state to a malleable state so that the material can be formed to a portion of a patient in need of support. Unfortunately, in order to heat the thermoplastic material in such a reaction, the material is placed in a separate and distinct heating bag where the exothermic reaction takes place. After appropriate heating, the thermoplastic material is removed from the bag and ready for use.

In addition, the assignee of the present invention has provided oxygen-based heaters and various packages for same. See, e.g., U.S. Pat. No. 7,722,782, issued on May 25, 2010; U.S. application Ser. No. 12/376,927, filed on Feb. 9, 2009; U.S. application Ser. No. 12/874,338, filed on Sep. 2, 2010; U.S. application Ser. No. 14/055,250 filed on Oct. 16, 2013; U.S. application Ser. No. 14/058,719, filed on Oct. 21, 2013; U.S. application Ser. No. 14/058,496, filed on Oct. 21, 2013; and, U.S. Ser. No. 13/734,594, filed Jan. 4, 2013, all of which are incorporated herein by reference.

These disclosed heaters and packages are successful at providing an oxygen based heater and/or package for same.

While the above disclosed devices and methods may be capable of providing effective formable splints or casts without the use of water, none of such devices disclose a single, integrated structure comprised of a thermoplastic material for use with a splint, or the like, and an oxygen activated heater constructed in association with the thermoplastic. The present invention is provided to solve these and other problems.

SUMMARY OF THE INVENTION

The present invention is directed to an integrated thermoformable splint and heater comprising a thermoplastic material having a top side and a bottom side opposite the top side and an oxygen activated heater operatively attached in association with at least one of the top and bottom sides of the thermoplastic material.

In a preferred embodiment of the invention, the oxygen activated heater includes a heater sheet, a wicking layer and an air diffuser layer each having a respective top surface and a bottom surface opposite their respective top surfaces. The bottom surface of the heater sheet is positioned in operative contact with at least one of the top or bottom sides of the thermoplastic material, and, the bottom surface of the wicking layer is positioned in operative contact with the top surface of the heater sheet. In this preferred embodiment, the bottom surface of the diffuser layer is positioned in operative contact with the top surface of the wicking layer. The wicking layer incorporates and distributes an electrolyte for operative use with the heater sheet upon exposure of the heater sheet to oxygen.

In another preferred embodiment of the invention, the heater sheet comprises a metal-based substrate that exothermically reacts with and upon exposure to oxygen.

In another preferred embodiment of the invention, the wicking layer is eliminated and the electrolyte is incorporated directly into the heater sheet.

In the preferred embodiment of the invention, at least one of the bottom surface of the heater sheet and the associated top or bottom side of the thermoplastic material includes a binding component there between. The binding component may include an adhesive and/or a non-woven fabric.

It is also contemplated that the invention includes a heat insulating material associated with the bottom side of the thermoplastic material.

It is also contemplated that the invention includes a heat insulating material associated with the top side of the heater. It is also contemplated that the air diffuser layer can serve as the heat insulating material on the top side of the heater sheet or wicking layer.

In still another preferred embodiment of the invention, the air diffuser layer includes a peripheral region around the entirety of the bottom surface of the air diffuser layer. This peripheral region is secured to a portion of the associated top or bottom side of the thermoplastic material, to, in turn, contain the heater sheet and wicking layer in operative association with the thermoplastic material.

The preferred embodiment of the invention includes an outer housing having an interior region and an outer surface. In this preferred embodiment, the oxygen activated heater and the thermoplastic material are contained within the interior region of the outer housing. The outer housing includes a seal and is made from a material that substantially precludes transfer of oxygen into the interior region of the outer housing.

In one preferred embodiment of the invention, the outer housing includes an oxygen penetration region and a removable seal over the oxygen penetration region. Oxygen is thus allowed to enter into the interior region of the outer housing, and, in turn, into contact with the oxygen activated heater upon at least partial displacement of the removable seal.

The present invention also includes a method for manufacturing an integrated thermoformable splint and heater comprising the steps of: fabricating an oxygen activated heater; attaching a thermoplastic material with the oxygen activated heater; positioning the attached thermoplastic material and oxygen activated heater within an interior region of a housing; and sealing the housing so as to preclude ingress of oxygen into the interior region of the housing, and, in turn, precluding activation of the oxygen activated heater.

In a preferred embodiment of the method, the step of fabricating an oxygen activated heater comprises the steps of: placing an electrolyte wicking layer on a top surface of metal based heater substrate, wherein the wicking layer includes a top surface and a bottom surface opposite the top surface; and, positioning an air diffuser layer over the electrolyte wicking layer so as to sandwich the electrolyte wicking layer between the air diffuser layer and the metal based heater substrate.

The thermoplastic material includes a top side and a bottom side opposite the top side. It is preferred that the method further includes the step of adhering the metal based heater substrate to the top side of the thermoplastic material. It is also preferred that the outer peripheral region of the air diffuser layer is secured to a portion of the top side of the thermoplastic material.

In another preferred embodiment of the method, the step of adhering the metal based heater to the top side of the thermoplastic material comprises the step of associating an adhesive or a non-woven felt with the top side of the thermoplastic material and a bottom surface of the metal based heater substrate.

In still another preferred embodiment, the method further includes the steps of: forming an oxygen penetration region into the outer housing for allowing ingress of ambient oxygen into the interior region of the housing, and, in turn, into contact with the oxygen activated heater; and, associating a removable seal over the oxygen penetration region so as to substantially preclude the ingress of oxygen into the interior region of the housing until the removable seal is displaced.

The present invention is also directed to a thermoformable splint kit comprising: a thermoplastic material having a top side and a bottom side opposite the top side; an oxygen activated heater operatively attached in association with at least one of the top and bottom sides of the thermoplastic material, wherein the thermoformable splint and oxygen activated heater are sealed within an oxygen impermeable housing; and, an elastic bandage for securing the thermofomable splint to a patient after it has been formed into a desirable configuration.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE DRAWINGS

Figure 1:
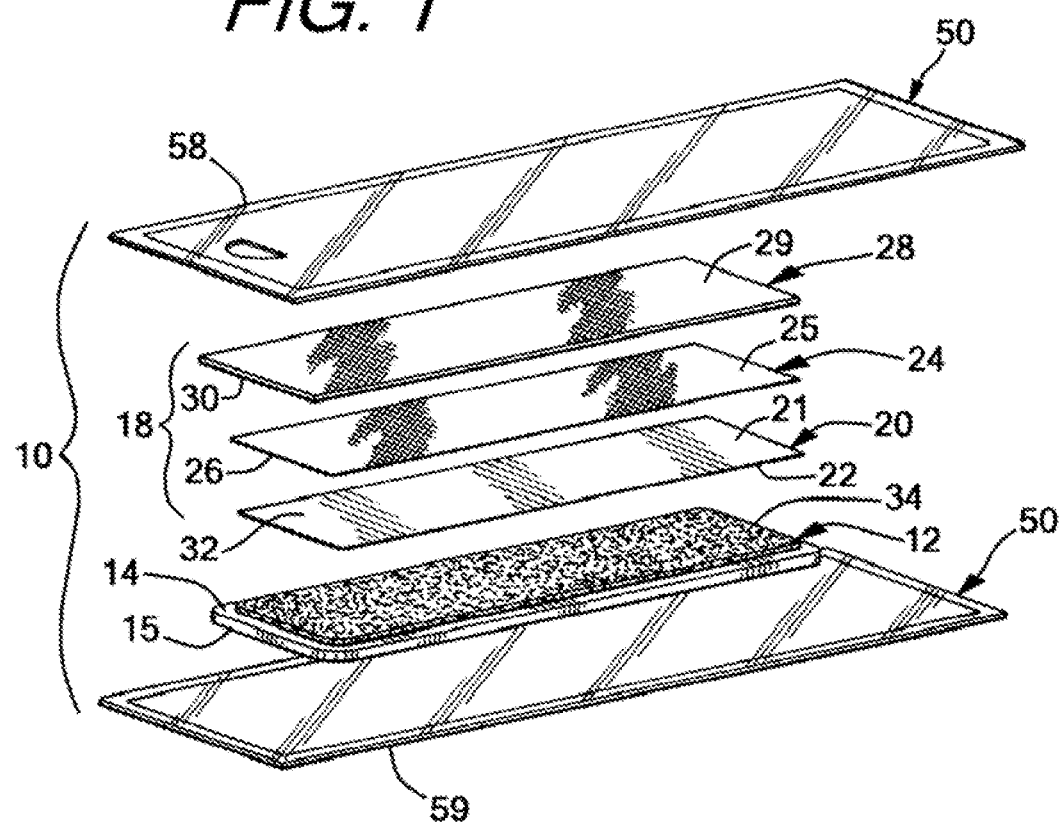
FIG. 1 of the drawings is an exploded view of the present invention.

The disclosure and the various features and advantageous details thereof are explained more fully with reference to the non-limiting embodiments and examples that are described and/or illustrated in the accompanying drawings and detailed in the following description. It should be noted that the features illustrated in the drawings are not drawn to scale, and features of one embodiment may be employed with other embodiments, as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the invention may be practiced and to further enable those of skill in the art to practice the examples of the disclosure. Accordingly, the examples and embodiments herein should not be construed as limiting the scope of the invention.

Integrated thermoformable splint and heater 10 is shown in FIG. 1 as comprising thermoplastic material 12 and oxygen activated heater 18. Thermoplastic material 12, which will result in a formable and rigid splint, has top side 14 and bottom side 15. As would be understood to those having ordinary skill in the art, the thermoplastic material is readily available from numerous sources and becomes malleable ("formable") upon heating to a predetermined temperature, such as approximately 210 degrees F. The thermoplastic material will revert back toward a rigid state as the temperature dissipates.

Oxygen activated heater 18 includes heater sheet 20, wicking layer 24 and air diffuser layer 28. Heater sheet 20, wicking layer 24 and air diffuser layer 28 each have a top surface and a bottom surface 21 and 22, 25 and 26, and, 29 and 30, respectively. The heater sheet comprises a metal-based substrate that exothermically reacts with and upon exposure to oxygen. Although the heater sheet is identified as a "sheet" or "substrate", it is contemplated by the present invention that the heater sheet can actually be applied as a layer, such as by deposition coating, rolling of material, etc.

Examples of the chemistry and general mechanical configurations associated with oxygen activated heaters are known in the art and specific examples have been incorporated herein by reference in the Background of the Invention. As will be readily understood by those having ordinary skill in the art with such heaters, wicking layer 24 serves to distribute the electrolyte evenly into the heater sheet. This electrolyte facilitates the reaction that takes place when the heater sheet is exposed to oxygen.

Figure 2:
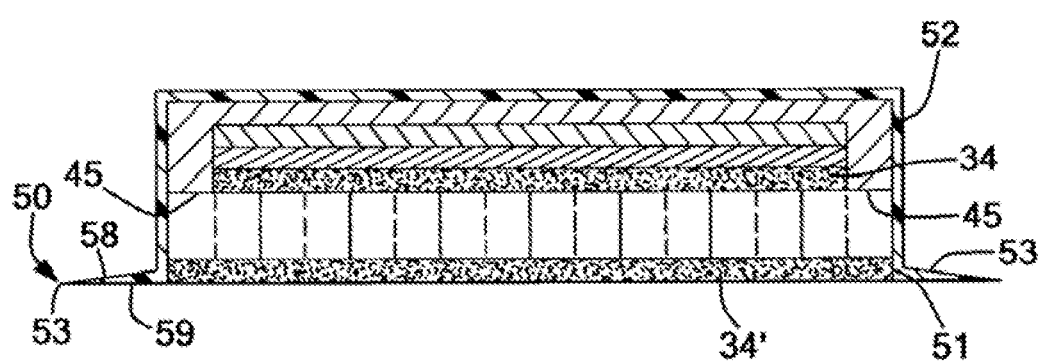
FIG. 2 of the drawings is an elevated cut-away view of the present invention.
Figure 3:
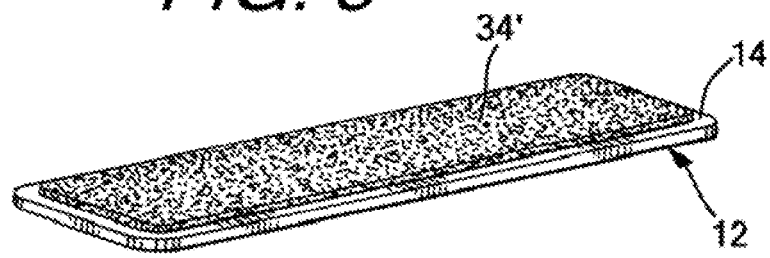
FIG. 3 of the drawings is a top perspective view of one of the features of the present invention.
Figure 5:
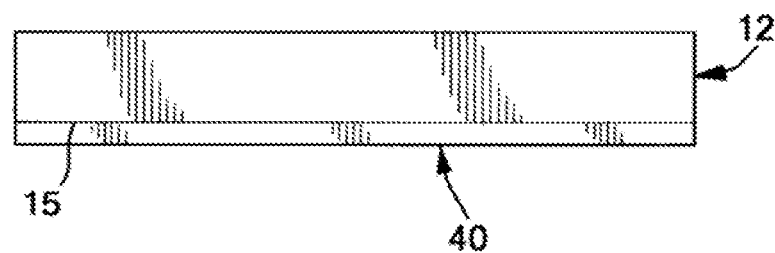
FIG. 5 of the drawings is an elevated side view of one of the features of the present invention.

As shown in greater detail in FIG. 2 (but as is also apparent in FIG. 1), bottom surface 22 of heater sheet 20 is operatively associated with top side 14 of thermoplastic material 12. Such association can occur as a result of chemical or mechanical bonding there between, or a combination thereof. For example, as shown in FIG. 1, top side of thermoplastic material 12 is associated with binding component 34. In this embodiment, the binding component comprises a non-woven fabric secured to the thermoplastic material. Although a non-woven fabric has been disclosed, other binding components are also contemplated by the present invention, including, but not limited to, adhesive materials, such as glue and double sided thermal tape. (See, for example, double sided thermal tape 34, shown in FIG. 3). In addition to the felt acting as a binding agent, desired felt may also include some heat insulating properties. Accordingly, it is contemplated that such felt, or other heat insulating material 40 (see FIG. 5) also be associated with bottom side 15 of thermoplastic material 12 inasmuch as the bottom side will be the side that comes into contact with the skin of a patient. Heat insulating material 40 in FIG. 5 can serve as a resilient pad, known as a cast pad, and is placed on bottom side 15 of thermoplastic material 12 for providing thermal protection while integrated thermoformable splint and heater 10 are being formed to the appropriate region of a patient, as well as providing comfort to the wearer after the thermoplastic heater reverts from a malleable state back to a rigid state.

As can be seen in FIGS. 1 and 2, bottom surface 26 of wicking layer 24 is operatively associated with and over top surface 21 of the heater sheet. Additionally, bottom surface 30 of air diffuser layer 28 is operatively positioned over top surface 25 of the wicking layer. As shown in FIG. 2, air diffuser layer (which allows relatively uniform dispersion of oxygen toward and in contact with the wicking layer, and, in turn, the heater sheet upon association with oxygen) includes peripheral region 45 as a result of it having a length and width greater than the length and width of the wicking layer and heater sheet. Accordingly, peripheral region 45 of air diffuser layer 28 is adhered to a portion of the top side of thermoplastic material 12. Such adherence secures/contains the heater sheet and wicking layer in operative association with the thermoplastic material.

As shown in FIGS. 1 and 2, integrated thermoformable splint and heater 10 further includes outer housing 50. The outer housing, once assembled about oxygen activated heater 18 and thermoplastic material 12, includes interior region 51 and outer surface 52 (see FIG. 2). As can be seen in FIG. 2, such an assembly is completely positioned within the interior region of the outer housing. As shown in FIGS. 1 and 2, outer housing 50 includes first and second sheets of material 58, 59, respectively. The first and second sheets of material are adhered at their edges (see FIG. 2) so as to form seal 53. The outer housing is fabricated from a material that is relatively impervious to oxygen transmission. One example of acceptable material for the outer housing is commercially available from Curwood Inc. P.O. Box 2968, 2200 Badger Ave., Osjkosh, Wis. 54903 under the trade name Liquiflex® A6661-MO. Seal 53 also is relatively impervious to oxygen transmission.

Figure 4:
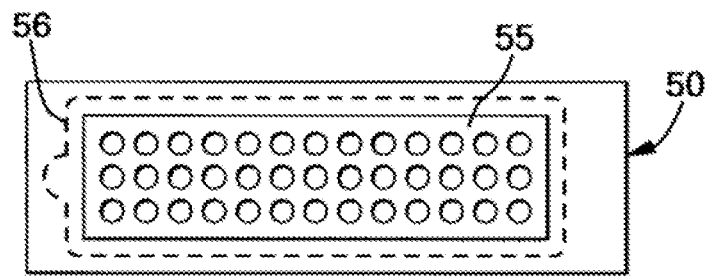
FIG. 4 of the drawings is a top view of one of the features of the present invention.

Outer housing 50 may include oxygen penetration region 55 and removable seal 56 operatively positioned over and around the oxygen penetration region, as shown in FIG. 4. The oxygen penetration region includes pores, or sections that will allow oxygen transmission into interior region 51 of the outer housing. However, removable seal 56 is comprised of a material (that may be the same as the material used for outer housing 50) that is intended to precluded oxygen transmission there through. Accordingly, oxygen will be precluded from entering interior region of the housing unless and until the removable seal is at least partially removed. Although outer housing has been described with an oxygen penetration region, it is also contemplated that such a region not be used. In such a case, oxygen will only be transmitted to the oxygen activated heater upon physical removal of the integrated heater and thermoplastic material from interior region 51 of the outer housing.

Integrated thermoformable splint and heater 10 is manufactured by fabricating oxygen activated heater 18 with air diffuser layer 28, wicking layer 24 and a metal-based (such as zinc) heater substrate 20, and securing all of them to thermoplastic material 12. As previously explained, the heater sheet is adhered to the thermoplastic material by means of a chemical and/or mechanical bond, such as with non-woven felt or an adhesive applied to top side 14 of the thermoplastic material. In addition, cast pad 40 (FIG. 5) may be applied to bottom side 15 of the thermoplastic material for thermal protection and comfort. As also previously explained, the air diffuser layer includes a peripheral region 45 that extends beyond the peripheries of the wicking layer and heating sheet. Inasmuch as the thermoplastic material has a length and width that is also greater than that of the wicking layer and heating sheet, the peripheral region 45 of the air diffuser layer can be secured to a portion of the thermoplastic material (see FIG. 2). In this instance, the heater sheet is held against the thermoplastic material by being "sandwiched" between the air diffuser and the thermoplastic material, and direct binding of the heater sheet to the thermoplastic material may not be required.

An outer housing 50 is fabricated from a flexible material that is relatively impermeable to oxygen. The outer housing is constructed to have a top sheet 58 and bottom sheet 59. Once constructed, the combined and integrated oxygen activated heater 18 (FIG. 1) and thermoplastic material 12 are positioned within what will become interior region 51 (FIG. 2) of the outer housing. The top and bottom sheet of the outer housing are then sealed together, optionally under a vacuum, forming seal 53 so that the interior region of the outer housing is substantially devoid of oxygen, and wherein the outer housing substantially conforms around the thermoplastic material and oxygen activated heater.

As an alternative embodiment, top sheet 58 of the outer housing can be fabricated with pores, or oxygen penetration regions 55, and a removable seal 56 positioned there over. As previously described, in such an embodiment, oxygen will only transmit into the interior region of the outer housing upon at least partial removal of the removable seal.

In operation, a desired user of the integrated thermoformable splint and heater would merely open the outer housing (by, for example, cutting a sealed edge with a scissors, or by tearing at a perforated line) and then removing the integrated thermoplastic material and oxygen activated heater there from. As oxygen from the ambient environment comes into contact with the air diffuser layer, and, in turn, into contact with the wicking layer, a chemical reaction will occur causing the heater sheet to create an exothermic reaction. This exothermic reaction will result in the release of heat from the heater sheet toward and into the thermoplastic material. Once the temperature is high enough, it will cause the thermoplastic material to deform, or become malleable. At that time, a person would then place the integrated device onto a person's arm (for example) and press the thermoplastic material against the person's arm until it forms thereto. Once properly formed, an elastic bandage, or the like, is wrapped around the person's arm and the integrated thermoplastic material and oxygen activated heater so as to secure it in place. Inasmuch as the side of the thermoplastic material applied to the person's arm includes an insulating pad (such as a cast pad) he or she will not be subjected to unsafe temperatures. The air diffuser layer also has heat insulating properties, so the person applying the device will also be protected from unsafe temperatures.

Shortly after the thermoplastic material has been properly formed, the exothermic reaction from the heater will cease and the elevated temperature of the thermoplastic material will quickly begin to dissipate. Such dissipation of heat will then cause the thermoplastic material to revert from a malleable (moldable) state, back toward a rigid state.

The integrated thermoformable splint and integrated heater is also fabricated as a kit. The kit includes the integrated thermoplastic material and oxygen activated heater associated securely positioned within the outer housing, and an elastic bandage.

Additional features, advantages, and embodiments of the invention may be set forth or apparent from consideration of the detailed description and drawings. Moreover, it is to be understood that the foregoing summary of the invention and the associated detailed description and drawings are exemplary and intended to provide further explanation without limiting the scope of the invention as claimed.

What is claimed is:

1. A thermoformable member comprising:
a rigid thermoplastic material having a top side and a bottom side opposite the top side, the thermoplastic material becoming malleable above a predetermined temperature and returning to a rigid state as the temperature dissipates; and
an oxygen activated heater operatively attached in association with at least one of the top side or the bottom side of the thermoplastic material, the oxygen activated heater heating the thermoplastic material to a temperature at least matching the predetermined temperature when activated.

2. The invention according to claim 1 wherein the oxygen activated heater comprises:
a heater sheet, an optional wicking layer and an air diffuser layer each having a respective top surface and a bottom surface opposite their respective top surfaces, wherein:
the bottom surface of the heater sheet is positioned in operative contact with at least one of the top side or the bottom side of the thermoplastic material;
the bottom surface of the wicking layer is positioned in operative contact with the top surface of the heater sheet; and
the bottom surface of the air diffuser layer is positioned in operative contact with the top surface of the wicking layer.

3. The invention according to claim 2, wherein at least one of the bottom surface of the heater sheet and the associated top or bottom side of the thermoplastic material includes a binding component therebetween.

4. The invention according to claim 3, wherein the binding component comprises a non-woven material.

5. The invention according to claim 3, wherein the binding component includes an adhesive.

6. The invention according to claim 2, wherein the heater sheet comprises a metal-based substrate that exothermically reacts with and upon exposure to oxygen.

7. The invention according to claim 2, wherein the wicking layer has been dosed with an electrolyte for operative use with the heater sheet upon exposure of the heater sheet to oxygen.

8. The invention according to claim 1, further including a heat insulating material associated with at least one of the top side or the bottom side of the thermoplastic material.

9. The invention according to claim 8, wherein the heat insulating material comprises at least one of the air diffuser layer and a heat insulating pad.

10. The invention according to claim 1, wherein the thermoplastic material is a splint.

11. A method for manufacturing a thermoformable member comprising the steps of:
fabricating an oxygen activated heater;
physically associating a thermoplastic material with the oxygen activated heater;
positioning the attached thermoplastic material and oxygen activated heater within an interior region of a housing; and
sealing the housing so as to preclude ingress of oxygen into the interior region of the housing, and, in turn, precluding activation of the oxygen activated heater.

12. The method according to claim 11, wherein the step of fabricating an oxygen activated heater comprises the steps of:
placing an electrolyte wicking layer on a top surface of a metal based heater substrate, wherein the wicking layer includes a top surface and a bottom surface opposite the top surface; and
positioning an air diffuser layer over the electrolyte wicking layer so as to sandwich the electrolyte wicking layer between the air diffusing layer and the metal based heater substrate.

13. The method according to claim 12, further comprises the step of securing an outer peripheral region of the air diffuser layer to a portion of a top side of the thermoplastic material.

14. The method according to claim 13, wherein the step of adhering the metal based heater to the top side of the thermoplastic material comprises the step of associating at least one of an adhesive and a non-woven felt with the top side of the thermoplastic material and a bottom surface of the metal based heater substrate.

15. The method according to claim 11, further including the steps of:
forming an oxygen penetration region into the outer housing for allowing ingress of ambient oxygen into the interior region of the housing, and, in turn, into contact with the oxygen activated heater; and
associating a removable seal over the oxygen penetration region so as to substantially preclude the ingress of oxygen into the interior region of the housing until the removable seal is displaced.

16. A thermoformable member comprising:
a thermoplastic material having a top side and a bottom side opposite the top side;
an oxygen activated heater operatively attached in association with at least one of the top side or the bottom side of the thermoplastic material; and
an outer housing having an interior region and an outer surface, wherein the oxygen activated heater and the thermoplastic material are contained within the interior region of the outer housing.

17. The invention according to claim 16, wherein the outer housing includes a seal and wherein the outer housing comprises a material that substantially precludes transfer of oxygen into the interior region of the outer housing.

18. The invention according to claim 17, wherein the outer housing includes an oxygen penetration region and a removable seal over the oxygen penetration region, wherein oxygen enters into the interior region of the outer housing, and, in turn, into contact with the oxygen activated heater upon at least partial displacement of the removable seal.

* * * * *